(12) United States Patent
Brieden et al.

(10) Patent No.: US 10,196,631 B2
(45) Date of Patent: Feb. 5, 2019

(54) CELL SEPARATION METHOD USING A RELEASE SYSTEM FOR CELL-ANTIBODY-SUBSTRATE CONJUGATES CONTAINING A POLYETHYLENE GLYCOL SPACER UNIT

(71) Applicant: Miltenyi Biotec GmbH, Bergisch Gladbach (DE)

(72) Inventors: Jennifer Brieden, Ennepetal (DE); Christian Dose, Bergisch Gladbach (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 186 days.

(21) Appl. No.: 15/166,675

(22) Filed: May 27, 2016

(65) Prior Publication Data

US 2016/0298105 A1    Oct. 13, 2016

Related U.S. Application Data

(63) Continuation-in-part of application No. 13/998,112, filed on Oct. 2, 2013, now abandoned.

(30) Foreign Application Priority Data

Oct. 23, 2012  (DE) ................. EP12189516

(51) Int. Cl.
  *C12N 13/00* (2006.01)
  *G01N 33/543* (2006.01)
  *G01N 33/569* (2006.01)

(52) U.S. Cl.
  CPC ....... *C12N 13/00* (2013.01); *G01N 33/54326* (2013.01); *G01N 33/569* (2013.01)

(58) Field of Classification Search
  CPC . C12N 13/00; G01N 33/54326; G01N 33/569
  See application file for complete search history.

(56) References Cited

U.S. PATENT DOCUMENTS

| | | | |
|---|---|---|---|
| 5,332,679 A | | 7/1994 | Simons et al. |
| 5,429,927 A | * | 7/1995 | Afseth ............. G01N 33/54326 435/2 |
| 5,518,882 A | | 5/1996 | Lund et al. |
| 2003/0003514 A1 | | 1/2003 | Kovalenko |
| 2007/0092558 A1 | | 4/2007 | Heavner et al. |
| 2008/0255004 A1 | * | 10/2008 | Neurauter ............. C40B 50/14 506/32 |
| 2014/0113315 A1 | * | 4/2014 | Brieden ............. G01N 33/532 435/7.24 |

OTHER PUBLICATIONS

Thermo Scientific "Avidin-Biotin Technical Handbook," published on Internet Mar. 23, 2009.*
Austin et al., "Proteomic analysis of the androgen receptor via MS-compatible purification of biotinylated protein on streptavidin resin," Proteomics, 2012, vol. 12, No. 1, pp. 43-53. Epub Dec. 12, 2011.*
Rampersand, "Novel discrete PEG-based crosslinking reagents for conjugation of antibodies and proteins to bioten, fluorochromes, enzymes and gold that eliminate aggregation, improves solubility, reduces non-specific binding and enhances low level detection limits," Molecular Biology of the Cell, vol. 22, 2011, p. 1931, Denver, CO, USA.
Ke, et al., "Avidin-Biotin-PEG-CPA Complexes as Potential EPR-directed Therapeutic Protein Carriers: Preparation and Characterization," Bioconjugate Chemistry, vol. 18, No. 5, Sep. 1, 2007, pp. 1644-1650.
Ke, et al., "Intermolecular Interaction of avidin and PEGylated biotin" Bioconjugate Chemistry, Ace, Washington, DC, vol. 18, No. 6, Nov. 21, 2007, pp. 2109-2114.

* cited by examiner

*Primary Examiner* — Galina Yakovleva
(74) *Attorney, Agent, or Firm* — Jaquelin K. Spong

(57) ABSTRACT

The invention is directed to a releasable conjugate comprising a biotinylated ligand having a biotin moiety, a ligand moiety (Ligand$_1$) and a biotin-binding molecule (bbm) bound to the biotin moiety of the biotinylated ligand. The ligand moiety of the biotinylated ligand may be separated by a spacer group consisting of polyethylene glycol. Furthermore, the invention relates to a method for cleaving the releasable conjugate by providing biotin or streptavidin and an auxiliary release agent in a sufficient concentration to displace the biotin-binding molecule (bbm) from the biotin moiety of the biotinylated ligand and a method for separation of target cells from a cell sample utilizing the conjugate.

12 Claims, 9 Drawing Sheets

CELL SEPARATION METHOD USING A RELEASE SYSTEM FOR CELL-ANTIBODY-SUBSTRATE CONJUGATES CONTAINING A POLYETHYLENE GLYCOL SPACER UNIT

CROSS REFERENCE TO RELATED APPLICATIONS

This application is a continuation-in-part from U.S. patent application Ser. No. 13/998,112, filed Oct. 2, 2013, and claims priority to European Application No. EP12189516.3, filed Oct. 23, 2012, the content of which are incorporated herein by reference in their entireties.

STATEMENT REGARDING FEDERALLY SPONSORED RESEARCH

Not applicable.

STATEMENT REGARDING MICROFICHE APPENDIX

Not applicable.

BACKGROUND

The present invention relates to a release system for cell-antibody-substrate conjugates; a method to selectively dissociate the conjugates, and a cell separation method using the release system.

The ability of biotin to bind streptavidin, avidin, and other biotin-binding molecules has been exploited for several decades, because of the high affinity, specificity, and broad applicability of this system.

To improve the release properties of biotin/streptavidin affinity systems, chemically modified biotin and streptavidin derivatives have been introduced, wherein only one or even both binding partners were modified. Such modifications lower the stability of the biotin/streptavidin complex by several orders of magnitude and thereby facilitate the dissociation of the two binding partners (see for example US 20080255004). Furthermore, mutated streptavidin proteins have been developed with reduced affinity for biotin or its analogues (M. Qureshi et al, J. Biol. Chem. 276 (2001) 46422-46428; T. Sano et al, Proc. Natl. Acad. Sci. USA 92 (1995) 3180-3184). U.S. Pat. No. 5,506,121 discloses so called "strept-tags" i.e. peptides with reduced binding affinity to streptavidin.

The modification of biotin or streptavidin is laborious. Since many reagents for the coupling of biotin with substrates, like antibodies, are commercially available, it is widely practiced to use unmodified biotin as labeling agent.

In this respect, U.S. Pat. No. 5,215,927 describes the isolation of target cells by contacting the desired cell population with a monoclonal antibody and subsequent incubation with a biotinylated anti-species immunoglobulin directed to the specific monoclonal antibody. The mixture is separated over a solid phase comprising immobilized avidin as biotin-binding molecule, which facilitates the immobilization of the target cells and separation of unlabeled targets. The desired cells are subsequently released by mechanical agitation to disrupt the immobilized complex.

The use of release mechanisms mediated by unselective enzyme degradation, chemical reactions, intense mechanical forces, high temperature, or strong saline conditions are undesirable for the separation of living cells, because it is important to preserve the cells' integrity and viability. Accordingly, mechanisms are desired that allow a rapid and selective release of the target cells at physiological conditions.

As an alternative to enzymatic or chemical cleavage or the use of modified biotin/streptavidin molecules, biotin/streptavidin systems can also be cleaved by a ligand competition mechanism. For example, a biotinylated molecule can be released from a streptavidin-support by adding an excess of free biotin, thereby replacing the biotinylated molecule.

Methods based on the competition of free biotin or streptavidin against the respective counterpart (streptavidin or biotin) are known in numerous variants. James Hirsch et al. give an overview of these techniques in Analytical Biochemistry 308 (2002) 343-357.

Furthermore, Ke Shan et al. disclose in "Avidin-Biotin-PEG-CPA Complexes as Potential EPR-Directed Therapeutic Protein Carriers: Preparation and Characterization", Bioconjugate Chemistry, vol. 18, no. 5, 1 Sep. 2007, pages 1644-1650 and "Intermolecular interaction of avidin and PEGylated biotin", Bioconjugate Chemistry, vol. 18, no. 6, 21 Nov. 2007, pages 2109-2114, the use of biotin for dissociation of the Avidin-Biotin-PEG-enzyme-complex.

The competition reaction of free biotin/streptavidin against the respective bound counterpart is disclosed in WO 92/16841 for analytical means. WO 92/16841 describes inter alia a method for detecting a reporter molecule, which is specifically bound to an analyte and an insoluble phase via a streptavidin/biotin-binding system. After the work-up procedure, the streptavidin/biotin binding system is cleaved by a displacement ligand and the released analyte is analytically detectable via the reporter molecule.

US 2008/0255004, U.S. Pat. No. 6,869,606, and U.S. Pat. No. 4,656,252 disclose biotinylated antibodies comprising modified biotin, wherein the biotin moiety and the antibody moiety of the biotinylated antibodies are separated by a spacer group consisting of an aryl, alkyl, or aminocaprolic acid group. The use of hydrophobic aryl or alkyl groups is expected to cause agglomeration in aqueous solutions. Since physiological conditions of biological systems usually require aqueous solutions, agglomeration is an eminent problem for techniques utilizing rather hydrophobic substances. Spacer molecules derived from aminocaprolic acid (so called "LC linker") possess a linear alkyl chain with residues that support homo- or heterofunctional bioconjugation chemistries.

U.S. Pat. No. 5,518,882 discloses a similar method, wherein target cells are bound to a solid support, for example magnetic particles. This allows a further enrichment by applying a magnetic field, which immobilizes the target cells coupled to the magnetic beads. The target cells can be released from the particles by cleaving the biotin-binding system with a displacement ligand. Preferably, the conjugate "(magnetic bead)-antibiotin-biotin-antibody-cell" is cleaved by adding free streptavidin in access, resulting in a "(magnetic bead)-antibiotin" and a "streptavidin-biotin-antibody-cell" conjugate.

In general, a competition reaction, i.e. the displacement of a first ligand with a second ligand, will only proceed until the equilibrium between the kinetics of the binding reaction of the first and second ligand is reached. The equilibrium depends on the respective binding forces and concentrations of the ligand and the thermodynamic conditions of the reaction. The known competition reactions to displace biotin by streptavidin therefore lead either to an uncompleted release or are difficult to control since the underlying kinetics are usually not known.

The present release systems are not fast or reliable enough for a process involving labeling of living cells, cell separation or detection and unlabeling of the target cells.

SUMMARY

It was therefore an object of the present invention to provide a reliable and highly efficient release system comprising a biotinylated antibody for detection of living cells and its use in a cell separation method.

It is found that the binding affinity of a labeled binding partner targeted to the biotin moiety of a biotinylated antibody can be adjusted by placing a biocompatible spacer molecule between the biotin moiety and the antibody, wherein the labeled binding partner is provided with a detection means. With such a conjugate, cells can be first labeled for identification or isolation and after identification or isolation, the label can be removed to unlabel the desired target cells.

Disclosed here is a releasable conjugate comprising a biotinylated ligand having a biotin moiety, a ligand moiety (Ligand$_1$) and a biotin-binding molecule (bbm) bound to the biotin moiety of the biotinylated ligand wherein the biotin moiety and the ligand moiety of the biotinylated ligand are separated by a spacer group consisting of polyethylene glycol. Release agents and methods for the conjugate are also disclosed.

The method for the separation of target cells from a cell sample may include incubating the cell sample with a releasable conjugate comprising a biotinylated ligand having a biotin moiety, a ligand moiety (Ligand$_1$) and a biotin-binding molecule (bbm) bound to the biotin moiety of the biotinylated ligand wherein the biotin moiety and the ligand moiety of the biotinylated ligand are separated by a spacer group consisting of polyethylene glycol according to the general formula I

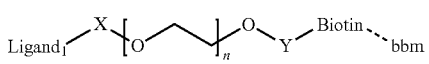

wherein n is between 1 and 500 inclusive, and wherein X and Y are substituted alkyl groups having between 1 and 20 carbon atoms inclusive with amine, amide, and/or thioether residues, wherein the ligand is a first antibody for which target cells express an antigen and the biotin-binding molecule (bbm) is a second antibody which comprises a magnetic particle as solid support. The method may then include applying a magnetic field to separate the cells labeled with the solid magnetic particle support from the cell sample by the applied magnetic field, adding a release agent in a sufficient concentration to displace the biotin-binding molecule (bbm) from the biotin moiety of the biotinylated ligand, wherein the release agent is added while the cells are in the presence of the magnetic field. The method may also include separating the target cells from the releasable conjugate while in the applied magnetic field.

These and other features and advantages are described in, or are apparent from, the following detailed description.

BRIEF DESCRIPTION OF THE DRAWINGS

Various exemplary details are described with reference to the following figures, wherein.

DETAILED DESCRIPTION

The object of the invention was therefore a releasable conjugate comprising a biotinylated ligand having a biotin moiety, a ligand moiety (Ligand$_1$) and a biotin-binding molecule (bbm) bound to the biotin moiety of the biotinylated ligand wherein the biotin moiety and the ligand moiety of the biotinylated ligand are separated by a spacer group consisting of polyethylene glycol according to the general formula I:

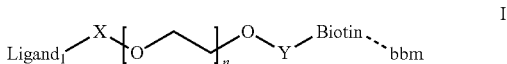

with n between 1 and 500 inclusive, and wherein X and Y are substituted alkyl groups having between 1 and 20 carbon atoms inclusive with amine, amide, and/or thioether residues, wherein the ligand is a first antibody and the biotin-binding molecule (bbm) is a second antibody which comprises a detection means selected from the group consisting of a chromophor unit, a fluorescence unit, a radioactive unit, and solid support The conjugate of formula I is dissociated by treatment with a release agent, which disrupts the interaction between the biotin and the biotin-binding molecule.

The release system of the invention is prepared by coupling a biotinylated ligand comprising a spacer group consisting of polyethylene glycol between the biotin and the ligand moiety with a biotin-binding molecule. The biotinylated ligand comprising the spacer group consisting of polyethylene glycol units might be coupled with one or several biotin-binding molecules and vice versa resulting in a releasable conjugate having one or more releasable cleavage sites. Accordingly, releasable conjugates of the invention may comprise biotinylated ligand, especially biotinylated antibodies carrying 1 to 20 biotin-binding molecules (bbm).

Preferably, the number n of glycol units in the polyethylene spacer is between 1 and 100, more preferred between 1 and 25, and most preferred between 1 and 10.

In a first, second, and third embodiment of the invention, the releasable conjugate has the structure according to general formula IIa, IIb, or IIc. In these embodiments, n stands for the number of glycol units as already disclosed.

scFv that have been synthesized by recombinant procedures including covalent and non-covalent conjugates containing these kind of molecules.

The term "release agent" refers to any compound capable of binding to the biotin moiety of the biotinylated ligand or the biotin-binding molecule thereby disrupting the interaction between the biotin moiety and the biotin-binding molecule. Suitable release agents are streptavidin or biotin. The preferred release agent in this invention is biotin. Suitable-modified streptavidin molecules are disclosed by James

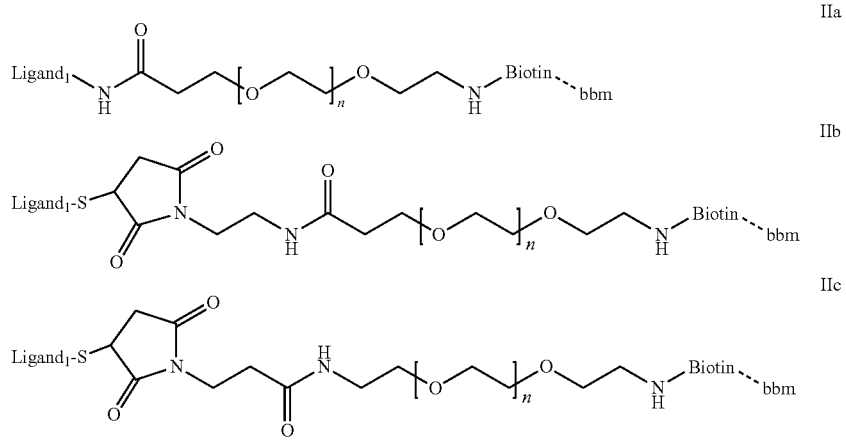

Figure 1:
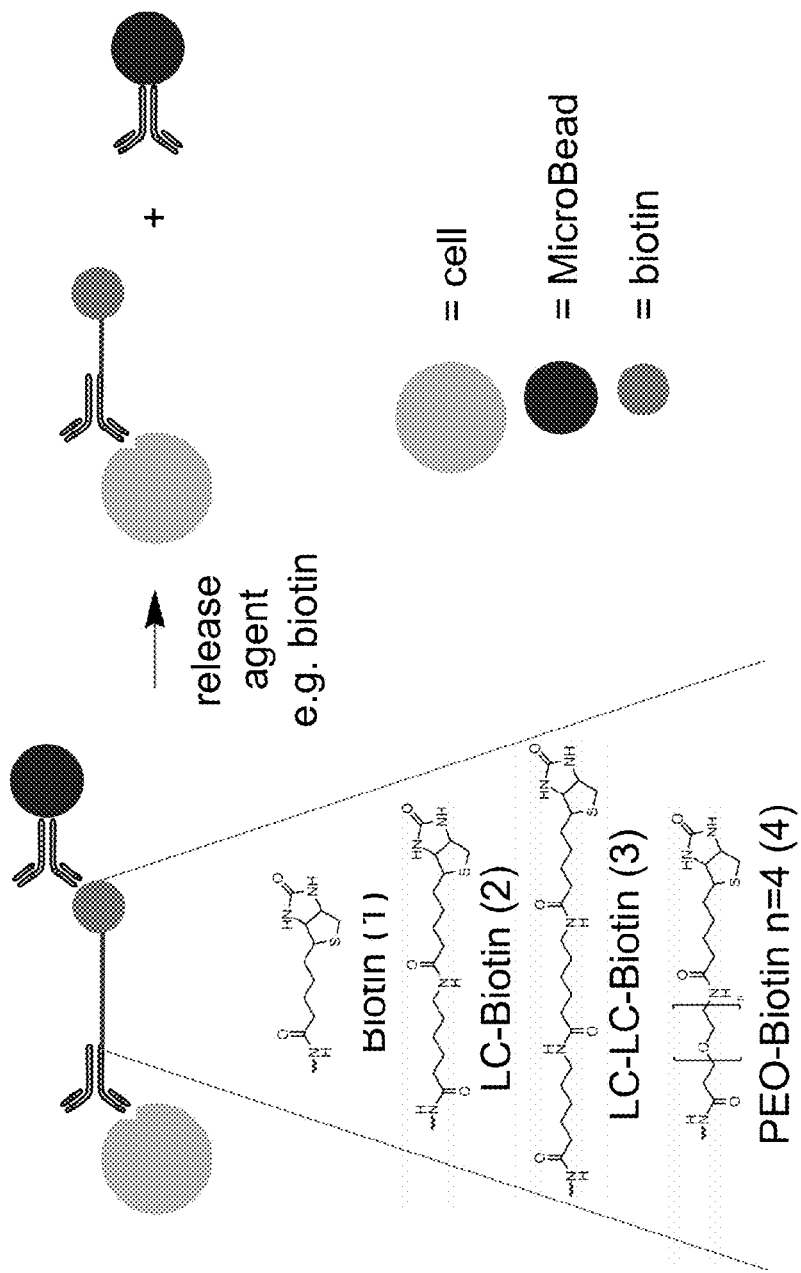
FIG. 1 shows conjugates containing Biotin (1), LC-Biotin (2), LC-LC-Biotin (3), and PEO-Biotin (4)

FIG. 1 shows conjugates according to the prior art containing Biotin (1), LC-Biotin (2), LC-LC-Biotin (3) (not according to the invention), and PEO-Biotin (4) (according to the invention). LC stands for "Long chain", a residue based on 6-aminocaproic acid; LC-LC stands for a double 6-aminocaproic acid spacer, while PEO stands for polyethylene oxide also known as polyethylene glycol.

The term "biotin" refers to 5-[(3aS,4S,6aR)-2-oxohexahydro-1H-thieno[3,4-d]imidazol-4-yl]pentanoic acid. The term "biotin" includes analogues or modified biotin compounds, which support similar host/guest interactions as unmodified biotin like, for example, iminobiotin, desthiobiotin, and DSB-X biotin. Preferably, unmodified biotin is used in the present invention.

The term "ligand" refers to any kind of antibody or fragmented antibody, directed against antigens expressed intracellularly or extra cellularly. The term relates to fully intact antibodies or fragmented antibody derivatives, e.g., Fab, Fab', F(ab')2, sdAb, scFv, di-scFv that have been synthesized by recombinant procedures including covalent and non-covalent conjugates containing these kind of molecules. Preferably, the term "ligand" refers to an antibody directed against antigen expressed by the target cells intracellular, like IL2, FoxP3, CD154, or extra cellular, like CD3, CD14, CD4, CD8, CD25, CD34, CD56, and CD133.

The term "biotin-binding molecule" (bbm) refers to an antibody, which is conjugated to a detection means and is displaceable from the biotin moiety of the biotinylated ligand by biotin or streptavidin. Preferably, the biotin-binding molecule (bbm) is an antibody selected from the class of immunoglobulin, e.g. IgG, IgA, IgM, IgD, IgE derived from animals, like e.g. mice, monkeys, goats, rabbits, sheep, or lamas. Furthermore, the term "biotin-binding molecule" (bbm) relates to fully intact or fragmented antibody derivatives, e.g., Fab, Fab', F(ab')2, sdAb, scFv, di- Hirsch et al. in Analytical Biochemistry 308 (2002) 343-357. Accordingly, the term "streptavidin and derivates thereof" refers to any molecule derived from streptavidin providing a binding affinity to biotin that is comparable to the binding affinity of unmodified streptavidin to biotin as well as to derivatives and conjugates of streptavidin without having the purpose of especially lowering the binding affinity to biotin.

The ligand, the biotin-binding molecule (bbm) and/or the release agent can be provided with a detection means, i.e. they may possess a label that can be used for detection. The detection means may, for example, emit a detection signal, like a chromophor unit, a fluorescence unit, or a radioactive unit. Suitable labeled release agents are commercially available, for example, under the trade names "anti-Biotin-PE" and "APC-Streptavidin" from Miltenyi Biotec GmbH, Germany and BioLegend Inc., respectively.

Furthermore, the detection means can be a solid-support, on which the biotin-binding molecule (bbm) and/or the ligand can be immobilized. The solid-support may be any of the known systems in biotechnology for immobilizing cells and can have the shape of particles, for example, sheets, plates, membranes, tubes, columns, wells, or micro arrays manufactured from various materials like polystyrene (PS), polymethylmethacrylate (PMMA), polyvinyl toluene (PVT), polyethylene (PE), or polypropylene (PP). Suitable materials are commercially available.

The solid support can further be a nano- to microscale magnetic particle, also known in the art as magnetic bead. The mean diameter of the beads can range from 10 nm to 10 μm. Biocompatible magnetic particles are commercially available and consist of, for example, forms of magnetic iron oxide coated by a shell of dextran molecules or silica. The solid support may also be polymers containing magnetic materials. Suitable particles are commercial available from Miltenyi Biotec GmbH, Germany under the trade name "MicroBeads" and "MACSiBeads" possessing a hydrodynamic diameter of 50-100 nm or 3-4 μm, respectively.

The use of the ligand, the biotin-binding molecule (bbm) and/or the release agent provided with a detection means allows a quantitative detection of the respective compound and/or of targeted cells and/or the separation or identification of the targeted cells.

According to this invention, magnetic particles can be used as solid-support to facilitate magnetic separation processes. For example, the biotin-binding molecule (bbm) can be coupled to a magnetic particle via a covalent coupling procedure. In this respect, the magnetic particles would act as a solid-support in separation protocols. Suitable magnetic particles conjugated with, for example anti-biotin antibodies and apparatus for magnetic separations of living cells are available from Miltenyi Biotec GmbH, Germany.

In a variant of the invention, the detection means comprises an antibody, which is used to bind the biotin-binding molecule (bbm). Such antibody-coupled detection means, especially antibody-coupled magnetic beads are commercially available.

This variant of the invention is illustrated by general formula IV, with $antibody_1$ targeted to a biomolecule of interest, $antibody_2$ as biotin-binding molecule, and $antibody_3$, coupled to a detection means, like a solid support, binding to $antibody_2$.

Alternatively, the utilization of an excess of, e.g., streptavidin as release agent forms a non-covalent complex with the biotinylated ligand, which results in a displacement of the biotin-binding molecule (VI).

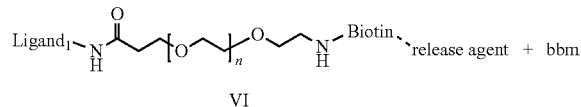

VI

The method of the invention is based on a competition reaction and will proceed until the binding equilibrium between the release agent, the biotin-binding molecule (bbm), and accordingly the biotin moiety is reached. The equilibrium depends on the respective binding forces, the concentration of the free release agent, and the thermodynamic conditions of the reaction. Accordingly, the term "sufficient amount to displace the second ligand by streptavidin or derivates thereof" does not stand for a specific value but needs to be evaluated according to the desired release rate.

For example, by utilizing an anti-biotin antibody as biotin-binding molecule (bbm) the releasable conjugate of the invention can be selectively cleaved by utilizing free biotin

IV

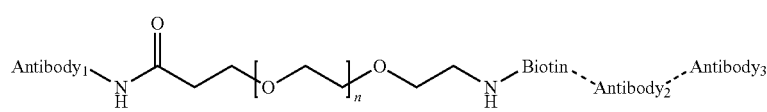

Suitable magnetic beads coupled to anti-IgG antibodies are commercially available from Miltenyi Biotec GmbH as "Anti-IgG MicroBeads".

Another object of the invention is a method for cleaving the releasable conjugate according to the invention as already disclosed wherein a release agent like biotin or streptavidin is provided in a sufficient concentration to displace the biotin-binding molecule (bbm) from the biotin moiety of the biotinylated ligand.

All embodiments and variants of the already disclosed releasable conjugate can be employed in the method of the invention.

The method of the invention results in the dissociation of the releasable conjugate between the biotin moiety and the anti-biotin antibody as biotin-binding molecule (bbm) as shown in figures V and VI. The releasable conjugate is selectively cleaved between the biotin moiety and the anti-biotin antibody by adding an excess of, for example, free biotin as release agent. The release agent forms a non-covalent complex with the biotin-binding molecule (bbm) and facilitates the release of the biotinylated ligand (V).

V

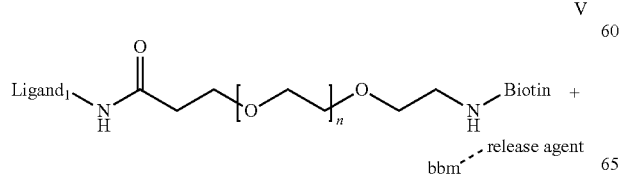

or streptavidin as release agent. If free biotin is used as release agent, a molar ratio (biotinylated ligand:free biotin) of 1:1,000 to 1:1,000,000, preferably a molar ratio of 1:1,000 to 1:100,000 is sufficient to dissociate the releasable conjugate. In case of streptavidin as release agent, a molar ratio (biotinylated ligand: streptavidin) of 1:1 to 1:10,000 preferably 1:10 to 1:1,000 may be provided to dissociate the releasable conjugate.

In another embodiment of the method of the invention, it was found that the addition of an auxiliary release agent improves the release efficiency method of the invention. In this embodiment, the release agent and an auxiliary release agent are provided in a sufficient concentration to displace the biotin-binding molecule (bbm) from the biotin moiety of the biotinylated ligand. Suitable auxiliary release agents have the general formulas VII, VIII, or IX:

VII

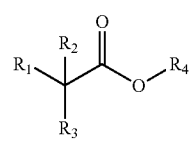

VIII

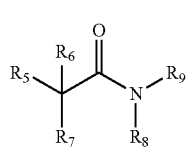

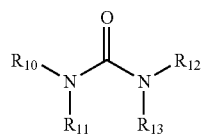

with $R_{1-3,5-13}$ chosen from the group consisting of hydrogen, substituted and unsubstituted alkyl residues having between 1 and 20 carbon atoms, inclusive, and $R_4$ chosen from the group consisting of substituted and unsubstituted alkyl residues having between 1 and 20 carbon atoms, inclusive.

The following compounds 7-15 illustrate specific examples of auxiliary release agents according to the invention. Not suitable as auxiliary release agent according to the invention is, for example, compound 15, despite its similar molecular structure in comparison to compounds 7-14. Accordingly, the auxiliary release agent may be chosen from the group consisting of at least one of the following 7-14 compounds:

| No. | Chemical structure |
|---|---|
| 7 | $H_2N-C(=O)-NH_2$ |
| 8 | methylurea dimethyl (N,N'-dimethylurea) |
| 9 | glycine methyl ester |
| 10 | glycinamide |
| 11 | N-acetylglycinamide |
| 12 | azidoacetamide |
| 13 | N-acetylglycine methyl ester |
| 14 | N-acetyl glutamine |

| No. | Chemical structure |
|---|---|
| 15 | glycine ($H_2N-CH_2-COOH$) |

The examples provide some insights regarding suitable conditions and resulting release efficiencies. In practice, the auxiliary release agent can be used in substantial excess in comparison to the release agent, for example with a molar ratio of 1:1,000 to 1:1,000,000 (release agent:auxiliary release agent).

It is another object of the invention to provide a method for separation of target cells from a cell sample comprising the steps:
a) incubating the cell sample with a releasable conjugate according to the invention, wherein the ligand is a first antibody for which the target cells express an antigen,
b) incubating the cell sample obtained in step a) with a second antibody coupled to a solid support,
c) separating the cells labeled with the a solid support obtained in step b) from the cell sample by applying an magnetic field,
d) adding a release agent in a sufficient concentration to displace the biotin-binding molecule (bbm) from the biotin moiety of the biotinylated ligand.

Accordingly, it is another object of the invention to provide a method for separation of target cells from a cell sample comprising the steps: incubating the cell sample with a releasable conjugate comprising a biotinylated ligand having a biotin moiety, a ligand moiety (Ligand,) and a biotin-binding molecule (bbm) bound to the biotin moiety of the biotinylated ligand wherein the biotin moiety and the ligand moiety of the biotinylated ligand are separated by a spacer group consisting of polyethylene glycol according to the general formula I

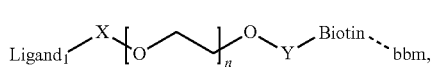

wherein n is between 1 and 500 inclusive, and wherein X and Y are substituted alkyl groups having between 1 and 20 carbon atoms inclusive with amine, amide, and/or thioether residues, wherein the ligand is a first antibody for which target cells express an antigen and the biotin-binding molecule (bbm) is a second antibody which comprises a magnetic particle as solid support.

The method may also include applying a magnetic field to separate the cells labeled with the solid magnetic particle support from the cell sample by the applied magnetic field, and adding a release agent in a sufficient concentration to displace the biotin-binding molecule (bbm) from the biotin moiety of the biotinylated ligand, wherein the release agent is added while the cells are in the presence of the magnetic field. The method may also include separating the target cells from the releasable conjugate while in the applied magnetic field. The auxiliary release agent may also be added to the sample while the cells are in the presence of the magnetic field. The addition of the auxiliary release agent may speed up the separating of the target cells from the releasable conjugate by addition of the auxiliary release agent.

All embodiments and variants of the already disclosed releasable conjugate can be employed in the method of the invention.

Optionally, subsequent to step d), in a further step e) the biotin-binding molecule (bbm) is separated from the target cells. The target cells may still be labeled with the conjugate according to the general formula I after separation.

The method according to the invention can be performed in step c) and optionally in step e) may include a separation of the labeled cells. To this end, the biotin-binding molecule of the releasable conjugate comprises a magnetic bead as solid support and the separation step is performed by applying a magnetic field. Magnetic cell sorting is known to the person skilled in the art and can be conducted in a permanent or an electromagnetic field with or without the use of a ferromagnetic column containing ferromagnetic material. Columns containing ferromagnetic material enhance the gradient of the magnetic field and are available from Miltenyi Biotec GmbH, Germany.

In this variant of the invention, the magnetically labeled cells are separated from the non-magnetic (i.e. non-labeled) cells by applying a magnetic field. After separation, the magnetic label can be removed by adding biotin or streptavidin with or without an auxiliary release agent in a sufficient concentration to displace the biotin-binding molecule (bbm) in step d). Accordingly, the biotin-binding molecule may be separated from the target cells in at least one column containing ferromagnetic material. Therefore, the separation step may take place in the magnetic field, such that separating the biotin-binding molecule from the target cells comprises applying a magnetic field to the target cells.

This release step can be performed within or outside of the magnetic field. For example, the magnetic labeled cells may be washed from the column and the magnetic label removed outside of the magnetic field. Alternatively, the magnetically labeled cells can be unlabeled by adding the release agent to the column located in the magnetic field. In this variant, the target cells (with the conjugate) are eluated from the column/ the magnetic fields whereas the magnetic label remains on the column and in the magnetic field.

In the optional step e), i.e., the separation of the biotin-binding molecule (bbm) from target cells can be achieved by centrifugation or preferably by applying a magnetic field, i.e., by magnetic cell sorting technique as already described. Step c) and e) are preferably conducted in at least one (the same) or especially in two different columns containing ferromagnetic material.

Especially for the quantitative detection of the target cells within the method of the invention, the ligand and/or the biotin-binding molecule (bbm) may preferentially comprise a chromophor or a fluorescence unit as detection means. The detection means of the ligand and/or the biotin-binding molecule (bbm) is detected subsequent to step d) to detect the target cells. Methods for cell detection, for example, fluorescence activated cell sorting (FACS) are known to the person skilled in the art.

It is furthermore an object of the invention to provide a kit comprising a biotinylated antibody, a biotin-binding molecule provided with a detection means, a release agent, and optionally an auxiliary release agent. The biotinylated antibody is selected according to the desired target cells, e.g., against a certain antigen. The kit according to the invention is used to first label the desired cells with the biotinylated antibody and then conjugating the biotin-binding molecule, which is optionally labeled or coupled to solid-support. After performing a separation step to yield the desired target cells, the release agent and optionally the auxiliary release agent are added to cleave the biotinylated antibody with the target cells from the biotin-binding molecule.

EXAMPLES

The examples and comparative examples show that the releasable conjugates and the method according to the invention allow a fast and reliable dissociation. Cells targeted by the releasable conjugates can be separated from cell suspensions and efficiently released, which enables a further processing of the isolated cells.

Example 1

Coupling of Anti-CD8-Biotin Conjugates and Cell Surface Staining

Coupling Protocol 1:

To prepare conjugates according to the first embodiment, IIa anti-CD8-antibody in PBS/EDTA-buffer was re-buffered to 100 mM $NaHCO_3$-buffer (pH 8.3). NHS-Biotin, NHS-LC-Biotin, NHS-LC-LC-Biotin, and NHS-PEO-Biotin (n=4, as shown in FIG. 1, available from Thermo Scientific/ Pierce) were dissolved in DMSO at concentration of 5 mg/mL and added in different molar ratios to the antibody solution at 2.5 mg/mL. After 1 h incubation time at room temperature, unreacted biotin was removed by gel filtration utilizing PBS/EDTA-buffer. Protein concentrations were determined by the absorbance at 280 nm. The approximate biotin to protein ratios (B/P) were determined by the standardized HABA-avidin-assay.

Coupling Protocol 2:

To prepare bioconjugates according to the second embodiment IIb or IIc anti-CD8-antibody was reduced with 10 mM DTT in MES-buffer. After 1 h incubation time at room temperature, the antibody was purified by gel filtration utilizing PBS/EDTA-buffer. To afford the anti-CD8-$PEO_4$-Biotin (5) (according to IIb) and anti-CD8-$PEO_2$-Biotin (6) (according to IIc) conjugates maleimide-$PEO_4$-Biotin or maleimide-$PEO_2$-Biotin (available from Thermo Scientific/ Pierce), respectively, were dissolved in PBS/EDTA-buffer at 5 mg/mL and added with a molar excess to the antibody solution at 2.5 mg/mL. After 15 h incubation at room temperature, the unreacted biotin was removed by gel filtration utilizing PBS/EDTA-buffer. Protein concentrations were determined by the absorbance at 280 nm. The approximate biotin to protein ratios (B/P) were determined by the standardized HABA-avidin-assay.

Cell surface staining with anti-CD8-Biotin conjugates: peripheral blood mononuclear cells (PBMCs) in PBS/ EDTA/BSA-buffer were stained for 10 min at 4° C. with 0.5 µg/mL of anti-CD8-Biotin (1), anti-CD8-LC-Biotin (2), anti-CD8-LC-LC-Biotin (3), or anti-CD8-PEO-Biotin (4) as illustrated in FIG. 1. The cells were washed with cold PBS/EDTA/BSA-buffer and stained for 10 min at 4° C. with an excess of anti-Biotin-PE. The cells were washed with cold PBS/EDTA-BSA-buffer and analyzed by flow cytometry.

Figure 2:
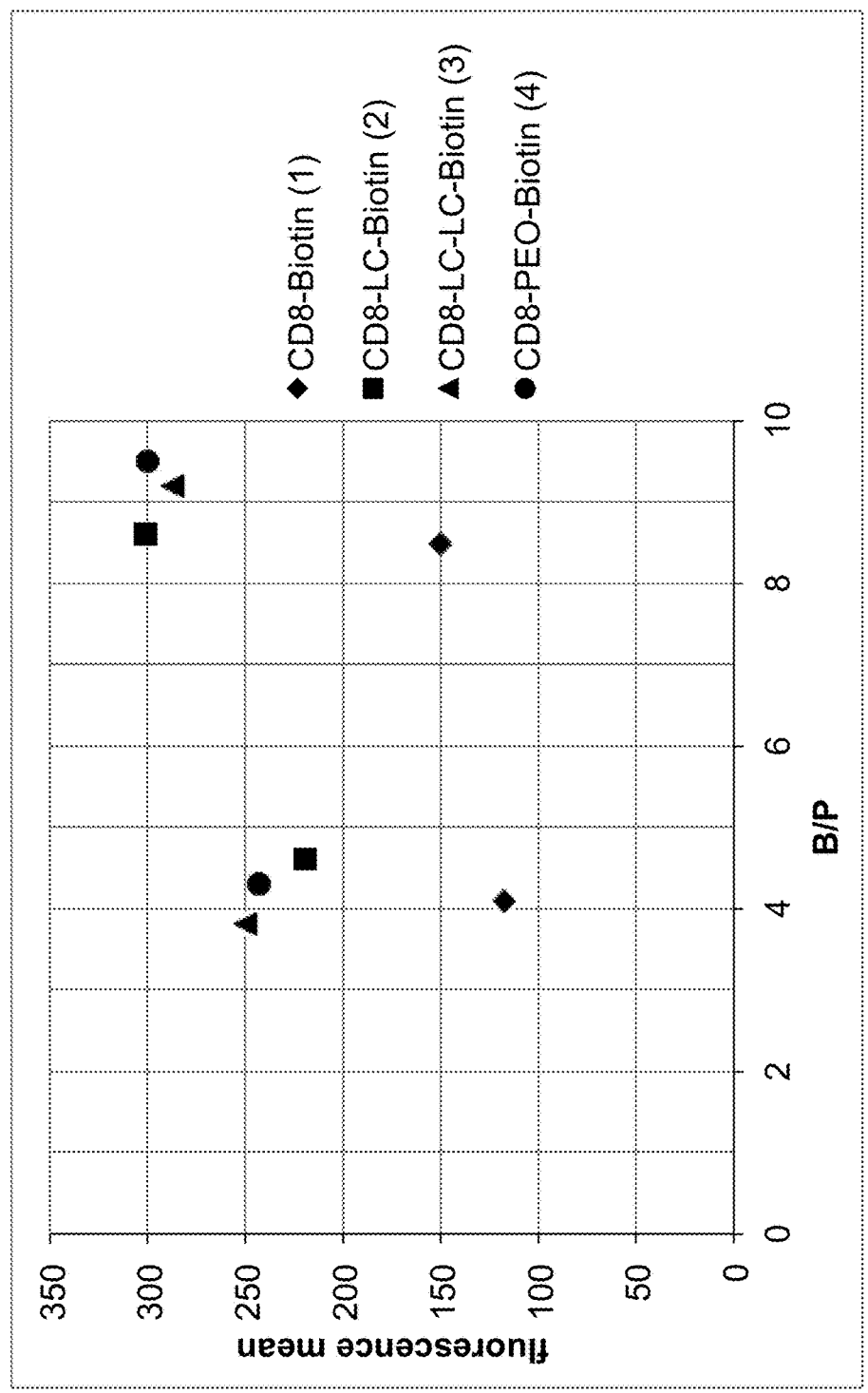
FIG. 2 shows the mean fluorescence intensities that have been achieved with different anti- CD8-Biotin conjugates as a function of the B/P ratio.

FIG. 2 shows the mean fluorescence intensities that have been achieved with different anti-CD8-Biotin conjugates as a function of the B/P ratio. Cell surface staining with anti-CD8-LC-Biotin (2), anti-CD8-LC-LC-Biotin (3), or anti-CD8-PEO-Biotin (4) furnished equally fluorescence signals. In contrast, cells stained with anti-CD8-Biotin (1) missing a spacer molecule between the biotin and the antibody moiety provided diminished mean fluorescence intensity although B/P ratio of the conjugates was comparable to the other biotinylated antibodies. These experiments illustrate the advantage of affinity systems containing spacer molecules as in anti-CD8-LC-Biotin (2), anti-CD8-LC-LC-Biotin (3), or anti-CD8-PEO-Biotin (4) in comparison to conjugates, like anti-CD8-Biotin (1) missing an additional linker between the biotin and antibody moiety.

Example 2

Cell Surface Staining with Anti-CD8-Biotin Conjugates and Kinetic Analysis

PBMCs in PBS/EDTA/BSA-buffer were stained for 10 min at 4° C. with 0.5 µg/mL of anti-CD8-Biotin (1), anti-CD8-LC-Biotin (2), anti-CD8-LC-LC-Biotin (3), anti-CD8-PEO-Biotin (4), anti-CD8-PEO-Biotin (5), or anti-CD8-PEO$_2$-Biotin (6). The cells were washed with cold PBS/EDTA/BSA-buffer and stained for 10 min at 4° C. with an excess of anti-Biotin-PE. The cells were washed with cold PBS/EDTA-BSA-buffer and incubated with 0.1 mM biotin at room temperature in the dark. The cells and the dissociation of anti-Biotin-PE was monitored by flow cytometry analysis after certain time points in relation to the starting sample missing release agent.

Figure 3:
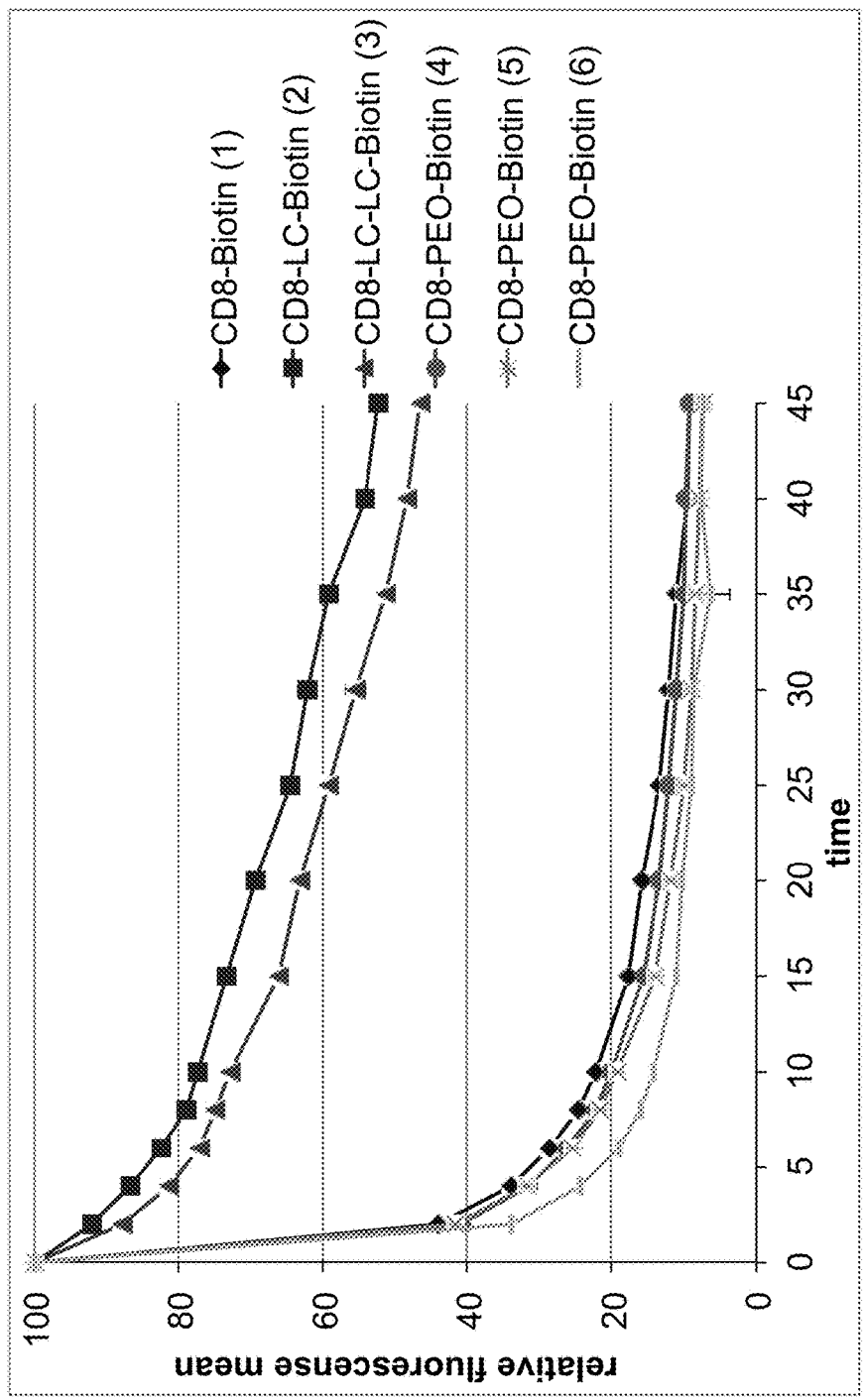
FIG. 3 shows the relative fluorescence signal of CD8 positive cells in the presence of different anti-CD8-Biotin conjugates.

FIG. 3 illustrate a fast decrease of the fluorescence signal of CD8 positive cells within the first 10 min reaction time in the presence of anti-CD8-Biotin (1), anti-CD8-PEO-Biotin (4), anti-CD8-PEO-Biotin (5), or anti-CD8-PEO$_2$-Biotin (6), while the dissociation rate in the case of anti-CD8-LC-Biotin (2) and anti-CD8-LC-LC-Biotin (3) was significant slower. These examples show that the release of conjugates comprising either no spacer molecule or spacer units according to the invention is much faster than with conjugates comprising a spacer molecule not according to the invention, like LC or LC-LC. It is important to note, that spacer molecules seem to be necessary to achieve equally cell stainings as already disclosed in FIG. 2.

Example 3

Cell Surface Staining with Anti-CD8-PEO-Biotin Conjugate and Kinetic Analysis CD8 positive cells in PBS/EDTA/BSA-buffer were stained for 10 min at 4° C. with 0.5 µg/mL anti-CD8-PEO-Biotin (4). The cells were washed with cold PBS/EDTA/BSA-buffer and stained 10 min at 4° C. with an excess of anti-Biotin-PE. The cells were washed with cold PBS/EDTA-BSA-buffer and incubated with different concentrations of the compounds 10, 12, and 15 at room temperature in the dark. The dissociation of the anti-CD8-PEO-Biotin/anti-Biotin-PE system was monitored by flow cytometry analysis after 10 min incubation time in relation to samples missing release agent.

Figure 4:
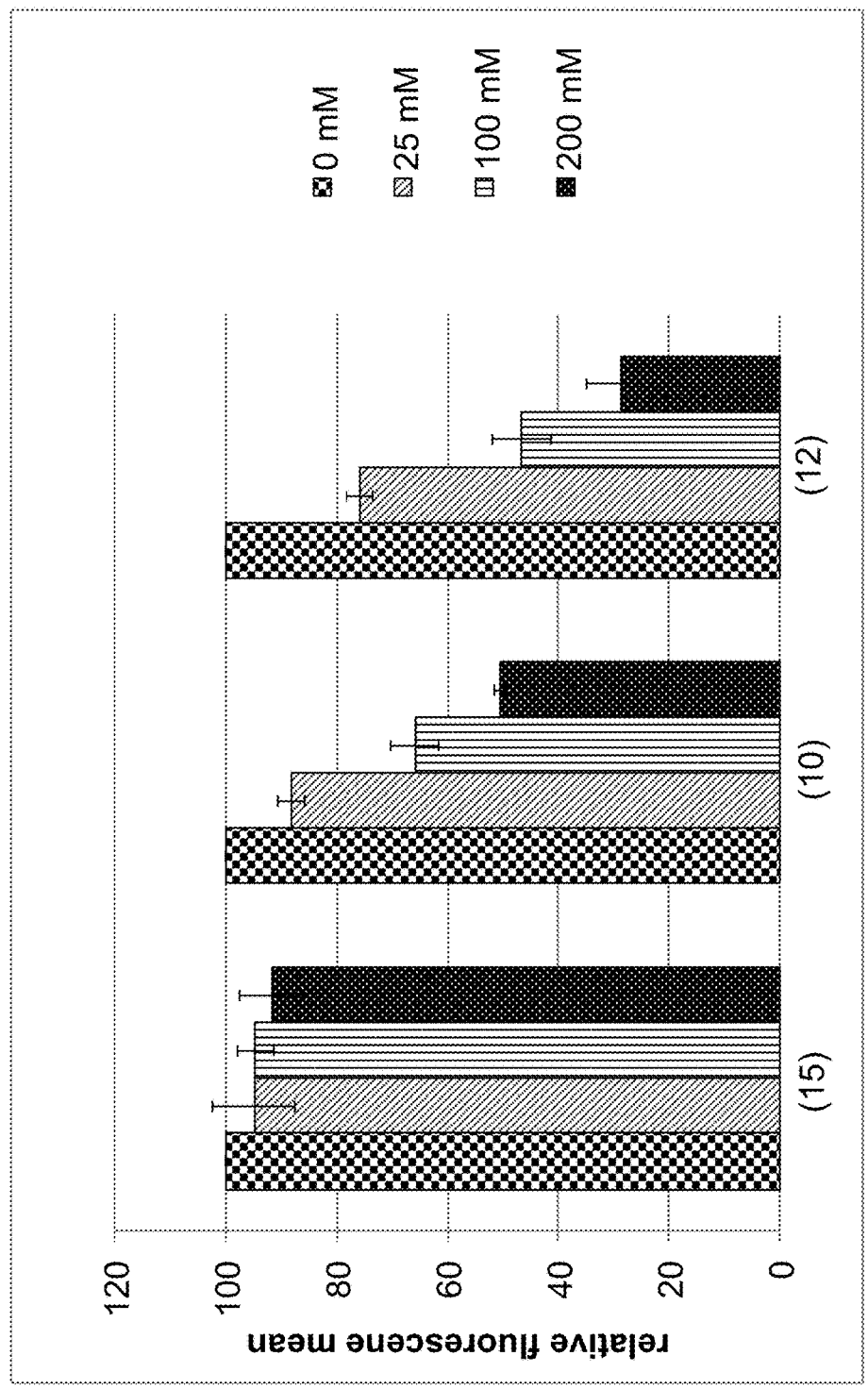
FIG. 4 shows the relative fluorescence signal of CD8 positive cells with different auxiliary release agents.

FIG. 4 illustrates that the compounds 10 and 12 highly facilitate the dissociation of the anti-CD8-PEO-Biotin/anti-Biotin-PE system in comparison to molecule 15, furnishing lower release yields. These examples show that auxiliary release agents according to the invention can facilitate the dissociation of the invented release.

Example 4

Cell Surface Staining with Anti-CD8-Biotin Conjugates and Kinetic Analysis

CD8 positive cells in PBS/EDTA/BSA-buffer were stained for 10 min at 4° C. with 0.5 µg/mL anti-CD8-LC-Biotin (3) and anti-CD8-PEO-Biotin (4). The cells were washed with cold PBS/EDTA/BSA-buffer and stained for 10 min at 4° C. with an excess of anti-Biotin-PE. The cells were washed with cold PBS/EDTA-BSA-buffer and incubated with different amounts of streptavidin in absence or in combination with compound 12 at 100 mM concentration. The dissociation of the anti-CD8-PEO-Biotin/anti-Biotin-PE and the anti-CD8-LC-LC-Biotin/anti-Biotin-PE systems were monitored by flow cytometry analysis after 10 min incubation times in relation to samples missing release agent.

Figure 5:
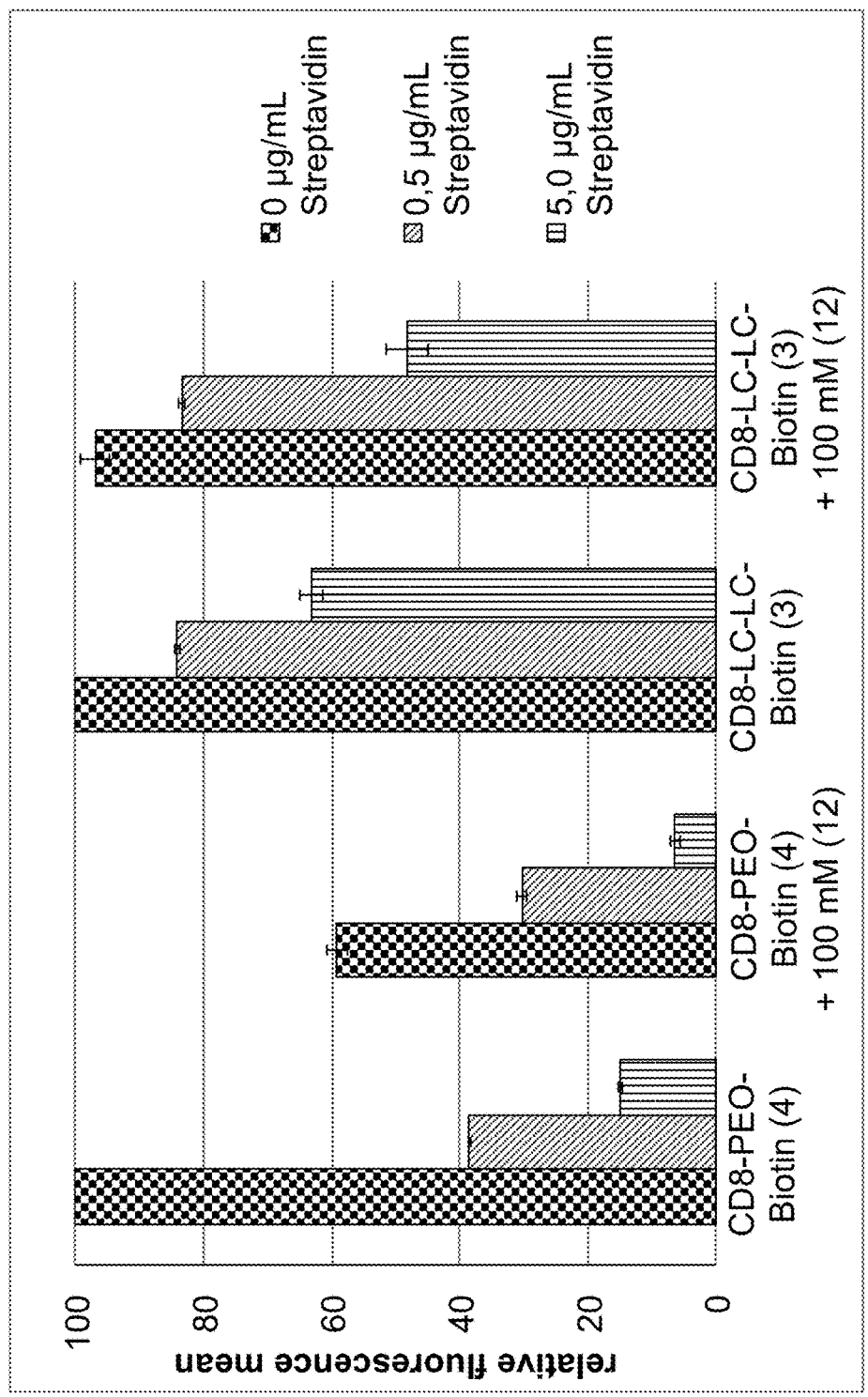
FIG. 5 illustrates the relative dissociation of the anti-CD8-PEO-Biotin/anti-Biotin-PE system compared to the anti-CD8-LC-LC-Biotin/anti-Biotin system in the presence of streptavidin.

FIG. 5 shows that the anti-CD8-PEO-Biotin/anti-Biotin-PE system dissociates significantly faster than the anti-CD8-LC-LC-Biotin/anti-Biotin-PE system in the presence of streptavidin. Moreover, the addition of compound 12 as auxiliary release agent accelerates the streptavidin-mediated dissociation process. This example shows that streptavidin on its own and in combination with compound 12 as auxiliary release agent can facilitate the dissociation of conjugates containing a spacer molecule according to the invention. In contrast, the dissociation of affinity systems possessing a spacer molecule not according to the invention, like LC-LC, is significantly less influenced by the utilization of the release agents.

Example 5

Cell Surface Staining with Anti-CD8-Biotin Conjugates and Kinetic Analysis

CD8 positive cells in PBS/EDTA/BSA-buffer were stained for 10 min at 4° C. with 0.5 µg/mL of anti-CD8-LC-LC-Biotin (3) and anti-CD8-PEO-Biotin (4). The cells were washed with cold PBS/EDTA/BSA-buffer and stained for 10 min at 4° C. with an excess of anti-Biotin-PE. The cells were washed with cold PBS/EDTA-BSA-buffer and incubated with different concentrations of allophycocyanin (APC)-labeled streptavidin (Biolegend, Inc.) in absence or in combination with compound 12. The dissociation of the anti-CD8-PEO-Biotin/anti-Biotin-PE and the anti-CD8-LC-LC-Biotin/anti-Biotin-PE systems were monitored by flow cytometry analysis after 10 min incubation times in relation to samples missing release agent.

Figure 6:
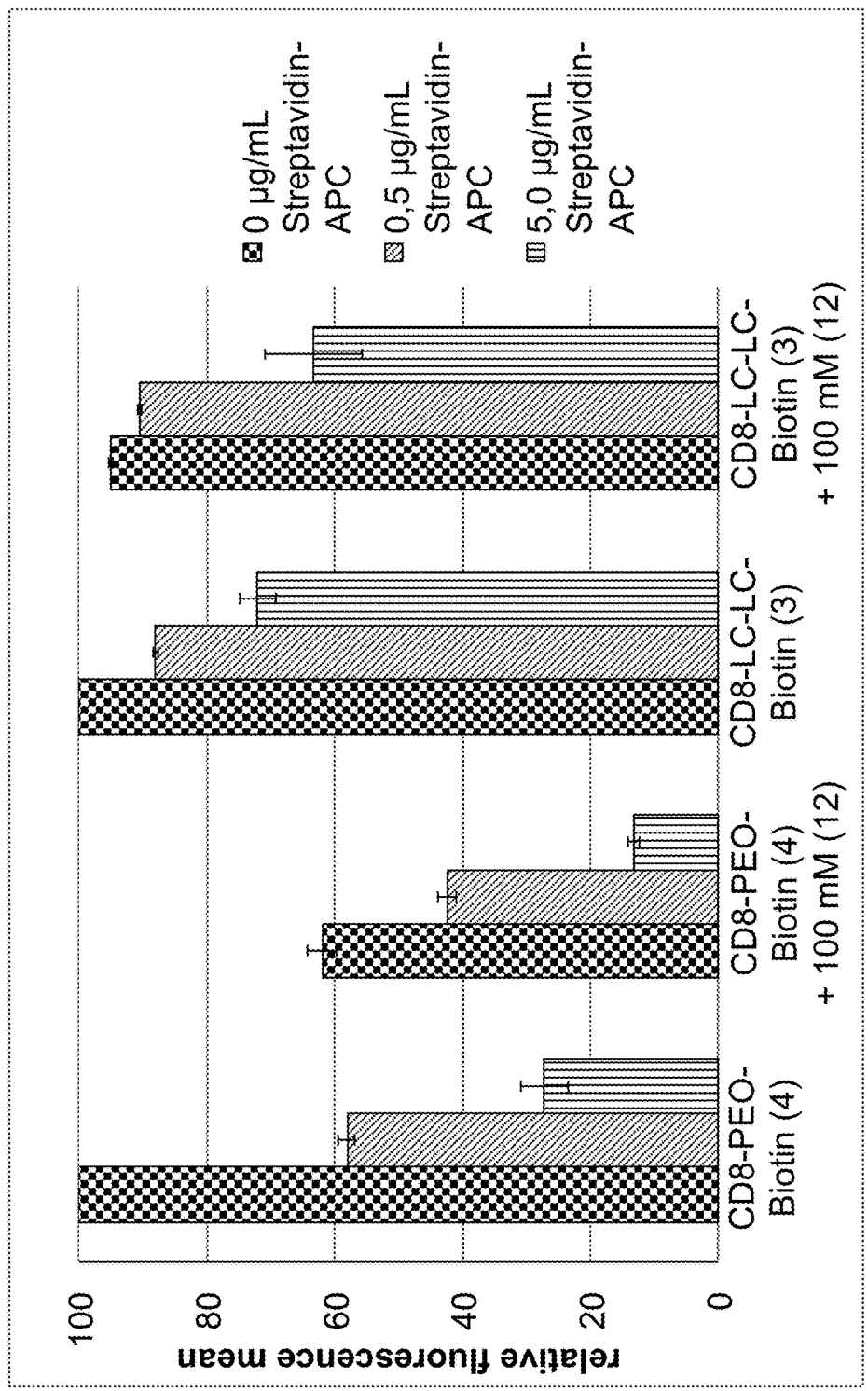
FIG. 6 illustrates the dissociation of the anti-CD8-PEO-Biotin/anti-Biotin-PE system compared to the anti-CD8-LC-LC-Biotin/anti-Biotin system in the presence of APC-streptavidin.

FIG. 6 shows that the anti-CD8-PEO-Biotin/anti-Biotin-PE system dissociates significantly faster than the anti-CD8-LC-LC-Biotin/anti-Biotin-PE system in the presence of APC-streptavidin. Moreover, the addition of compound 12 as auxiliary release agent accelerates the APC-streptavidin-mediated dissociation process. This example shows that APC-streptavidin on its own and in combination with compound 12 as auxiliary release agent can facilitate the dissociation of releasable conjugates containing a spacer molecule according to the invention. In contrast, the release agents significantly less influence the dissociation of affinity systems possessing a spacer molecule not according to the invention, like the anti-CD8-LC-LC-Biotin/anti-Biotin-PE system.

Example 6

Magnetic Cell Separation with Anti-CD8-PEO-Biotin Conjugate

PBMCs in PBS/EDTA/BSA-buffer were incubated at 4° C. for 10 min with anti-CD8-LC-LC-Biotin (3) and anti-CD8-PEO-Biotin (4). The cells were washed with cold PBS/EDTA/BSA-buffer and incubated for 15 min at 4° C. with anti-Biotin-MicroBeads (Miltenyi Biotec GmbH) and for 5 min at 4° C. with anti-CD8-PE. The cells were washed with cold PBS/EDTA-BSA-buffer and resuspended in 500 µL of cold buffer. The cell suspension was applied on a MS-column (Miltenyi Biotec GmbH) in a magnetic field for magnetic cell separation. The flow-through was collected as magnetically unlabeled cell fraction. The cells were washed within the magnetic field and the column was removed from the separator prior to the elution of the cells with 1 mL of cold PBS/EDTA/BSA-buffer. The isolated cell fraction was incubated for 10 min at different concentrations of biotin. The cell suspension was applied onto a second column and flow-through was collected as eluted cells. Cells retained on the column were eluted with 500 µL of cold PBS/EDTA/BSA-buffer in absence of the magnetic field. The amount of CD8 positive cells in the isolated fractions was determined by flow cytometry analysis. The percentage allocation of the eluted cells was calculated as follows:

$$\frac{\text{amount of cells in the eluted fraction}}{\text{amount of cells in the eluted fraction} + \text{amount of cells in the fraction retained by magnetic field}}$$

Figure 7:
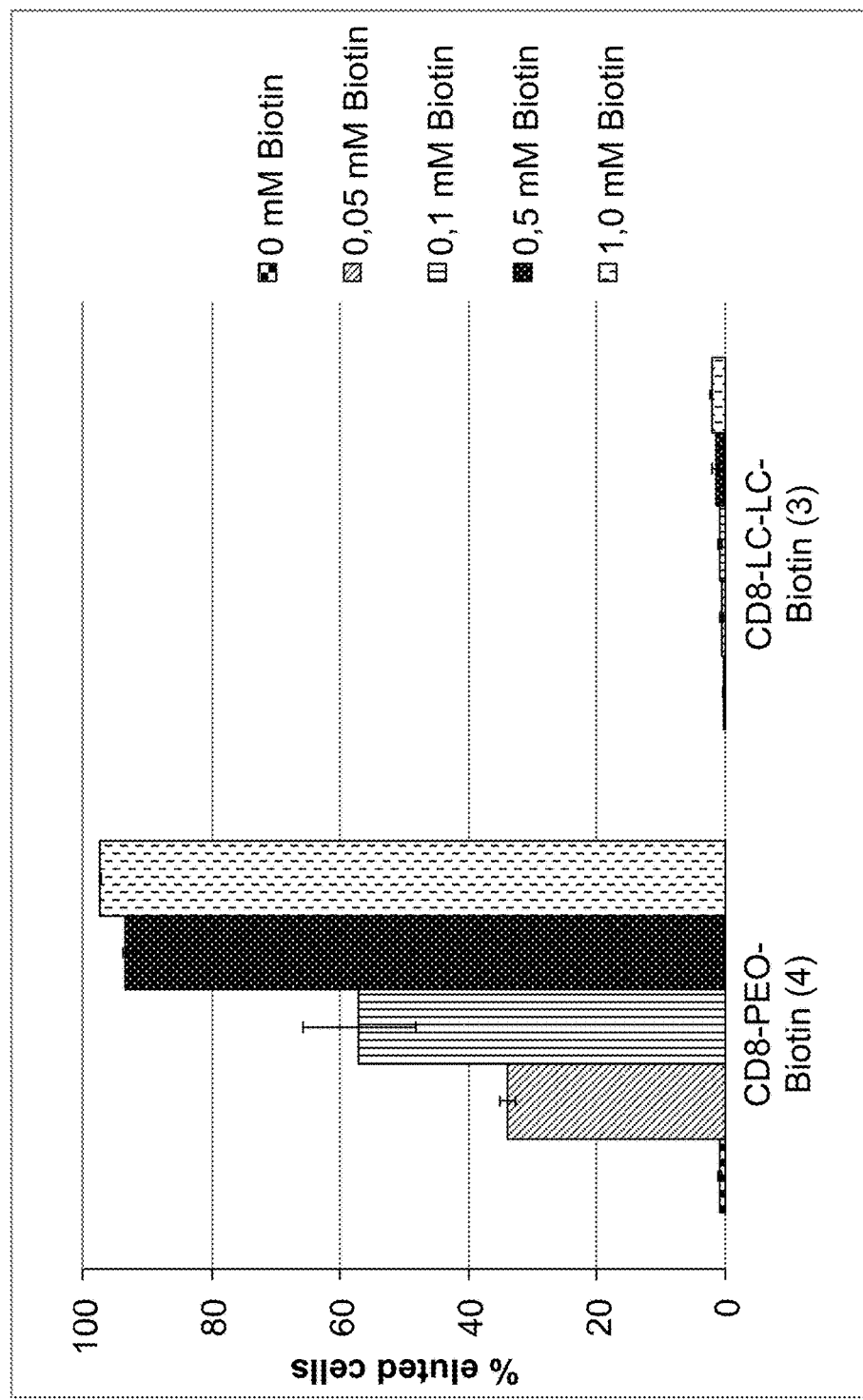
FIG. 7 is a comparison of magnetically labeled anti-CD8-PEO-Biotin/anti-Biotin system to the anti-CD8-LC-LC-Biotin/anti-Biotin system with the addition of biotin as release agent.

FIG. 7 illustrates that the incubation of cells labeled by the anti-CD8-PEO-Biotin/anti-Biotin-MicroBead system according to the invention with biotin leads to a significantly better release of the magnetic label in comparison to the anti-CD8-LC-LC-Biotin/anti-Biotin-MicroBead system. This example shows the possibility to efficiently release the magnetic labeling of separated cells in the anti-CD8-PEO-Biotin/anti-Biotin-MicroBead system by the addition of biotin as release agent.

Example 7

Magnetic Cell Separation with Anti-CD8-PEO-Biotin Conjugate

PBMCs in PBS/EDTA/BSA-buffer were incubated for 10 min at 4° C. with anti-CD8-LC-LC-Biotin (3) and anti-CD8-PEO-Biotin (4). The cells were washed with cold PBS/EDTA/BSA-buffer and incubated for 15 min at 4° C. with anti-Biotin-MicroBeads (Miltenyi Biotec GmbH) and for 5 min at 4° C. with anti-CD8-PE. The cells were washed with cold PBS/EDTA-BSA-buffer and resuspended in 500 µL of cold buffer. The cell suspension was applied on a MS-column in a magnetic field for magnetic cell separation. The flow-through was collected as magnetically unlabeled cell fraction. The cells were washed within the magnetic field and the column was removed from the separator prior to elution of the cells with 1 mL of cold PBS/EDTA/BSA-buffer. The isolated cell fraction was incubated for 10 min at different concentrations of streptavidin with and without compound 12. The cell suspension was applied onto a second column and flow-through was collected as eluted cells. Cells retained by the column were eluted with 500 µL of cold PBS/EDTA/BSA-buffer in absence of the magnetic field. The amount of CD8 positive cells in the isolated fractions was determined by flow cytometry analysis. The percentage allocation of the eluted cells was calculated as follows:

$$\frac{\text{amount of cells in the eluted fraction}}{\text{amount of cells in the eluted fraction} + \text{amount of cells in the fraction retained by magnetic field}}$$

Figure 8:
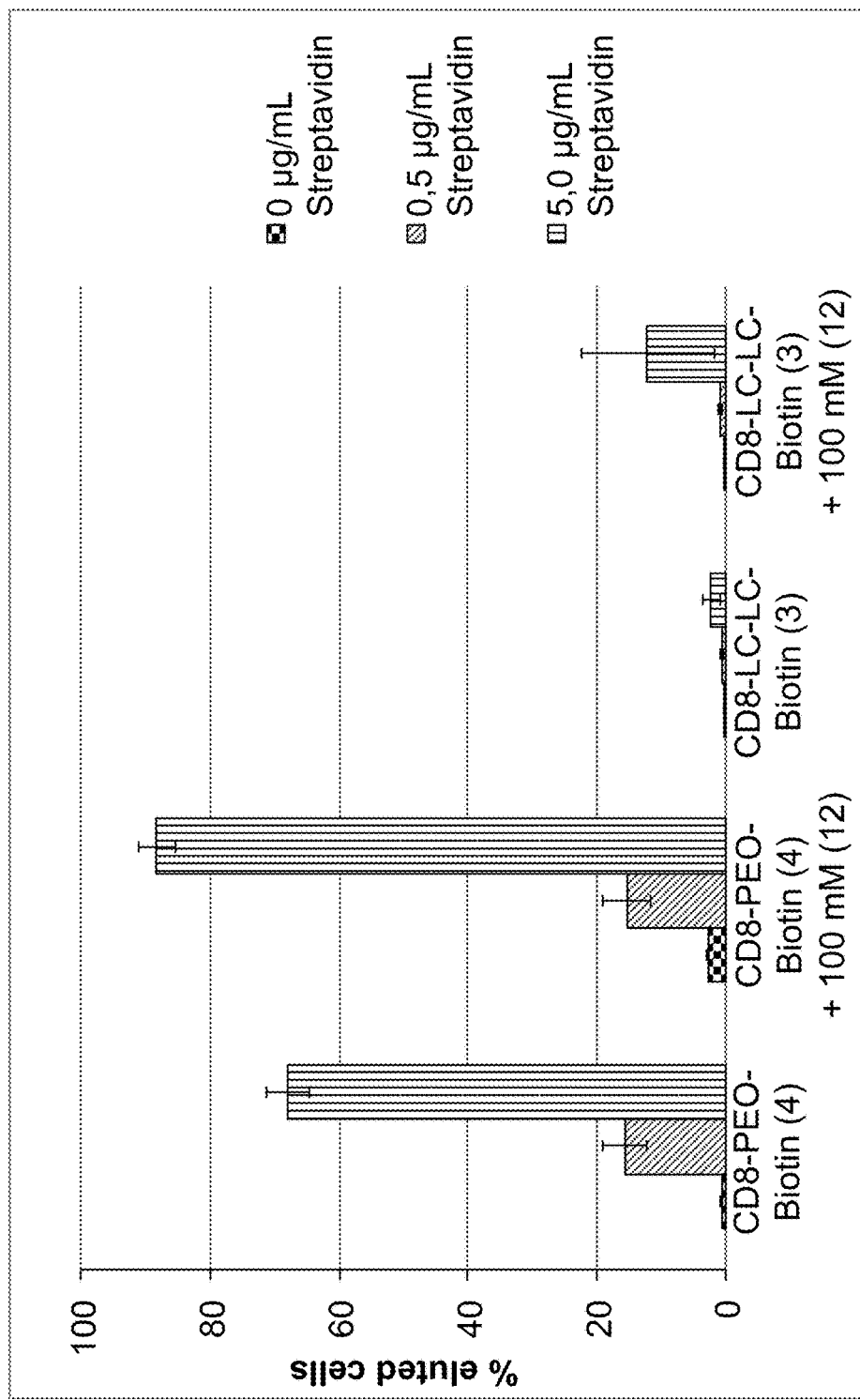
FIG. 8 is a comparison of the magnetically labeled anti-CD8-PEO-Biotin/anti-Biotin system to the anti-CD8-LC-LC-Biotin/anti-Biotin system in the presence of streptavidin.

FIG. 8 illustrates that the incubation of cells labeled by the anti-CD8-PEO-Biotin/anti-Biotin-MicroBead system according to the invention with streptavidin provides a significantly faster release of the magnetic label in comparison to the anti-CD8-LC-LC-Biotin/anti-Biotin-MicroBead system. Moreover, the addition of compound 12 to streptavidin as release agent further improves the dissociation of the CD8-PEO-Biotin/anti-Biotin-MicroBead system. This example shows that the use of an auxiliary release agent according to the invention can significantly improve the release efficiency.

Example 8

Magnetic Cell Separation with Anti-CD8-PEO-Biotin Conjugate

PBMCs in PBS/EDTA/BSA-buffer were incubated for 10 min at 4° C. with anti-CD8-LC-LC-Biotin (3) and anti-CD8-PEO-Biotin (4). The cells were washed with cold PBS/EDTA/BSA-buffer and incubated for 15 min at 4° C. with anti-Biotin-MicroBeads and for 5 min at 4° C. with anti-CD8-PE. The cells were washed with cold PBS/EDTA-BSA-buffer and resuspended in 500 µL of cold buffer. The cell suspension was applied on a MS-column in a magnetic field for magnetic cell separation. The flow-through was collected as magnetically unlabeled cell fraction. The cells were washed within the magnetic field and the column was removed from the separator prior to elution of the cells with 1 mL of cold PBS/EDTA/BSA-buffer. The isolated cell fraction was incubated for 10 min at different concentrations of APC-streptavidin with and without compound 12. The cell suspension was applied onto a second column and flow-through was collected as eluted cells. Cells retained by the column were eluted with 500 μL of cold PBS/EDTA/BSA-buffer in absence of the magnetic field. The amount of CD8 positive cells in the isolated fractions was determined by flow cytometry analysis. The percentage allocation of the eluted cells was calculated as follows:

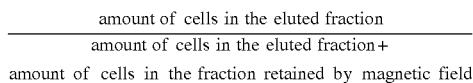

Figure 9:
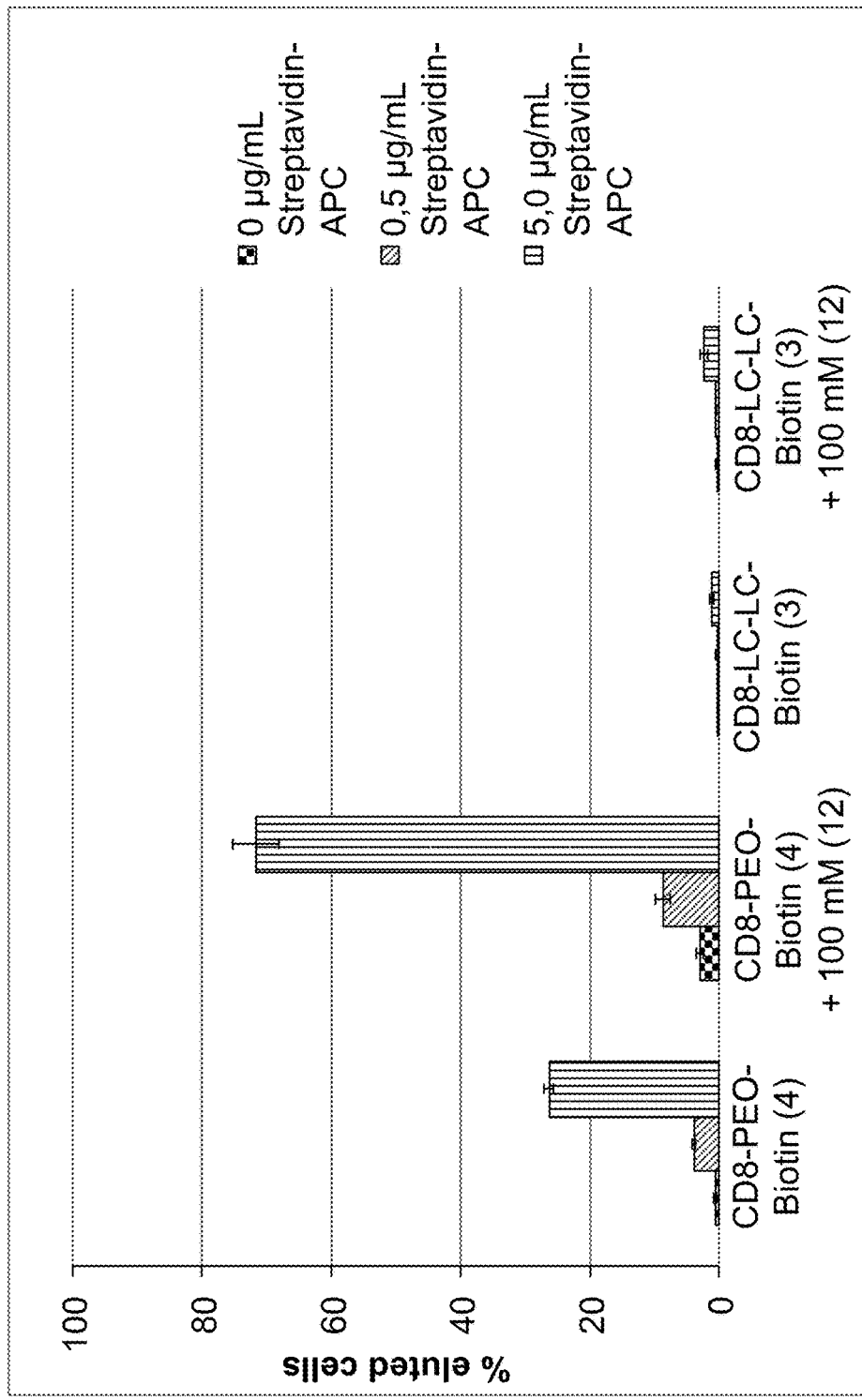
FIG. 9 is a comparison of the magnetically labeled anti-CD8-PEO-Biotin/anti-Biotin system to the anti-CD8-LC-LC-Biotin/anti-Biotin system in the presence of APC streptavidin.

FIG. 9 illustrates that cells labeled by the anti-CD8-PEO-Biotin/anti-Biotin-MicroBead system according to the invention and treated with APC-streptavidin as release agent are significantly faster eluted from the magnetic field in comparison to cells labeled with the anti-CD8-LC-LC-Biotin/anti-Biotin-MicroBead system. Moreover, the addition of compound 12 to APC-streptavidin as release agent further improves the dissociation of the CD8-PEO-Biotin/anti-Biotin-MicroBead system. These results demonstrate that the use of auxiliary release agent according to the invention can significantly improve the release efficiency.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A method for the separation of target cells from a cell sample comprising the steps:
   incubating the cell sample with a releasable conjugate comprising a biotinylated ligand having a biotin moiety, a ligand moiety ($Ligand_1$) and a biotin-binding molecule (bbm) bound to the biotin moiety of the biotinylated ligand wherein the releasable conjugate has the formula

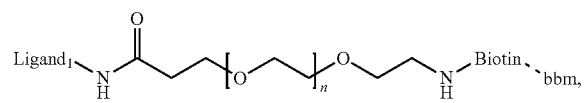

wherein n=1, and wherein the ligand moiety is a first antibody for which the target cells express an antigen and the biotin-binding molecule (bbm) is a second antibody which comprises a magnetic particle as a magnetic particle solid support;

applying a magnetic field to separate the target cells labeled with the solid magnetic particle support from the cell sample by the applied magnetic field;
   removing the solid magnetic particle support from the target cell labeled with the solid magnetic particle support by adding a release agent in a sufficient concentration to displace the biotin-binding molecule (bbm) from the biotin moiety, wherein the release agent is added while the target cells are in the presence of the magnetic field; and
   eluating the target cells comprising the biotinylated ligand moiety from the magnetic field whereas the magnetic particle solid support remains in the magnetic field.

2. The method of claim 1, further comprising adding an auxiliary release agent to the cell sample, wherein the auxiliary release agent is added while the cells are in the presence of the magnetic field.

3. The method of claim 2, wherein the ratio of the release agent to the auxiliary release agent is a molar ratio between about 1:1,000 and 1:1,000,000 release agent:auxiliary release agent.

4. The method of claim 2, wherein the release agent and the auxiliary release agent are provided in a sufficient concentration to displace the biotin-binding molecule (bbm) from the biotin moiety of the biotinylated ligand.

5. The method of claim 2, where in the auxiliary release agent is selected from the group consisting of the following 7-14 compounds:

7 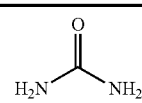

8 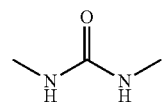

9 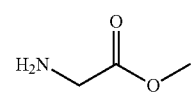

10 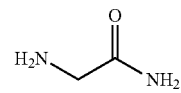

11 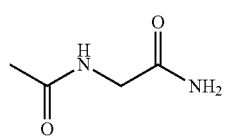

12 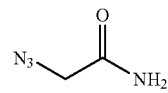

13 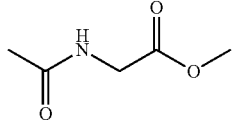

14 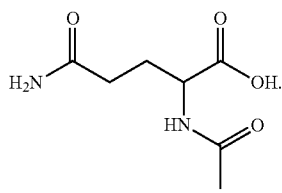

6. The method of claim 1, wherein the release agent is at least one selected from the group consisting of biotin and streptavidin.

7. The method of claim 1, wherein removing the solid magnetic particle support from the target cell labelled with the solid magnetic particle support is conducted in a column containing a ferromagnetic material.

8. The method of claim 1, wherein the antigen is expressed intracellularly or extracellularly.

9. The method of claim 1, further comprising detecting at least one of the biotinylated ligand and the biotin-binding molecule (bbm) subsequent to separating the target cells.

10. The method of claim 9, wherein detecting the at least one of the biotinylated ligand and the biotin-binding molecule (bbm) comprises using at least one selected from the group consisting of a chromophore unit, a fluorescence unit, and a radioactive unit as a detection means.

11. A method for the separation of target cells from a cell sample comprising the steps:
incubating the cell sample with a releasable conjugate comprising a biotinylated ligand having a biotin moiety, a ligand moiety (Ligand$_1$) and a biotin-binding molecule (bbm) bound to the biotin moiety of the biotinylated ligand wherein the releasable conjugate has the formula

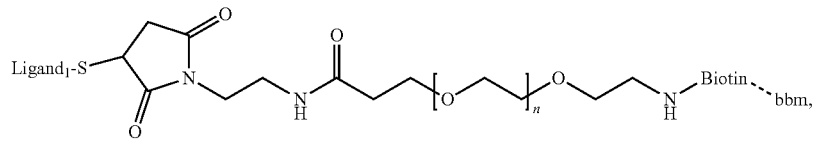

wherein n=1, and wherein the ligand moiety is a first antibody for which the target cells express an antigen and the biotin-binding molecule (bbm) is a second antibody which comprises a magnetic particle as a magnetic particle solid support;

applying a magnetic field to separate the target cells labeled with the solid magnetic particle support from the cell sample by the applied magnetic field;

removing the solid magnetic particle support from the target cell labeled with the solid magnetic particle support by adding a release agent in a sufficient concentration to displace the biotin-binding molecule (bbm) from the biotin moiety, wherein the release agent is added while the target cells are in the presence of the magnetic field; and eluating the target cells comprising the biotinylated ligand moiety from the magnetic field whereas the magnetic particle solid support remains in the magnetic field.

12. A method for the separation of target cells from a cell sample comprising the steps:
incubating the cell sample with a releasable conjugate comprising a biotinylated ligand having a biotin moiety, a ligand moiety (Ligand$_1$) and a biotin-binding molecule (bbm) bound to the biotin moiety of the biotinylated ligand wherein the releasable conjugate has the formula

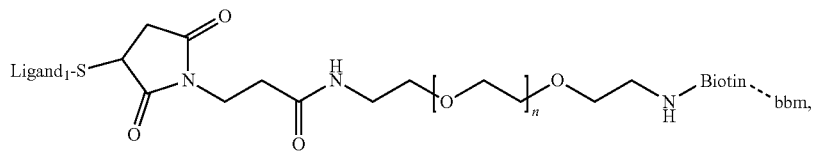

wherein n=1, and wherein the ligand moiety is a first antibody for which the target cells express an antigen and the biotin-binding molecule (bbm) is a second antibody which comprises a magnetic particle as a magnetic particle solid support;

applying a magnetic field to separate the target cells labeled with the solid magnetic particle support from the cell sample by the applied magnetic field;

removing the solid magnetic particle support from the target cell labeled with the solid magnetic particle support by adding a release agent in a sufficient concentration to displace the biotin-binding molecule (bbm) from the biotin moiety, wherein the release agent is added while the target cells are in the presence of the magnetic field; and eluating the target cells comprising the biotinylated ligand moiety from the magnetic field whereas the magnetic particle solid support remains in the magnetic field.

* * * * *